(12) United States Patent
Verkaart et al.

(10) Patent No.: US 6,508,778 B1
(45) Date of Patent: Jan. 21, 2003

(54) SYSTEM FOR WITHDRAWAL OF BLOOD

(75) Inventors: Wesley H. Verkaart, Duxbury, MA (US); Thomas G. Crimi, West Islip, NY (US)

(73) Assignee: Harvest Technologies Corporation, Plymouth, MA (US)

( * ) Notice: Subject to any disclaimer, the term of this patent is extended or adjusted under 35 U.S.C. 154(b) by 0 days.

(21) Appl. No.: 09/701,424

(22) Filed: Nov. 29, 2000

Related U.S. Application Data
(60) Provisional application No. 60/087,398, filed on Jun. 1, 1998.

(51) Int. Cl.[7] .................................................. A61M 5/00
(52) U.S. Cl. ....................... 604/6.15; 604/6.07; 604/6.1; 137/625.41
(58) Field of Search .............................. 604/6.15, 6.07, 604/6.1; 137/625.41

(56) References Cited

U.S. PATENT DOCUMENTS

| | | | |
|---|---|---|---|
| 2,804,075 A | * 9/1957 | Borden | 604/269 |
| 3,276,472 A | * 10/1966 | Jinkens et al. | 137/556 |
| 4,950,230 A | * 8/1990 | Kendell | 604/28 |
| 5,078,688 A | 1/1992 | Lobodzinski et al. | 605/164 |
| 5,593,385 A | 1/1997 | Harrison et al. | 604/83 |
| 5,665,061 A | * 9/1997 | Antwiler | 604/4 |
| 5,713,878 A | 2/1998 | Moutafis et al. | 604/283 |
| 5,725,511 A | 3/1998 | Urrutia | 604/280 |
| 5,795,340 A | 8/1998 | Lang | 604/283 |
| 5,807,312 A | 9/1998 | Dzwonkiewicz | 604/30 |
| 5,817,068 A | * 10/1998 | Urrutia | 137/625.41 |
| 5,853,382 A | * 12/1998 | Kingsley et al. | 604/4 |

* cited by examiner

Primary Examiner—A. Michael Chambers
(74) Attorney, Agent, or Firm—Clark & Brody

(57) ABSTRACT

The invention comprises a disposable tubing set (4) for connection to a rigid canister (2) that is maintained at a controlled reduced (vacuum) pressure. The set is used for collecting and anti-coagulating a patient's blood for later re-infusion into the same patient

13 Claims, 1 Drawing Sheet

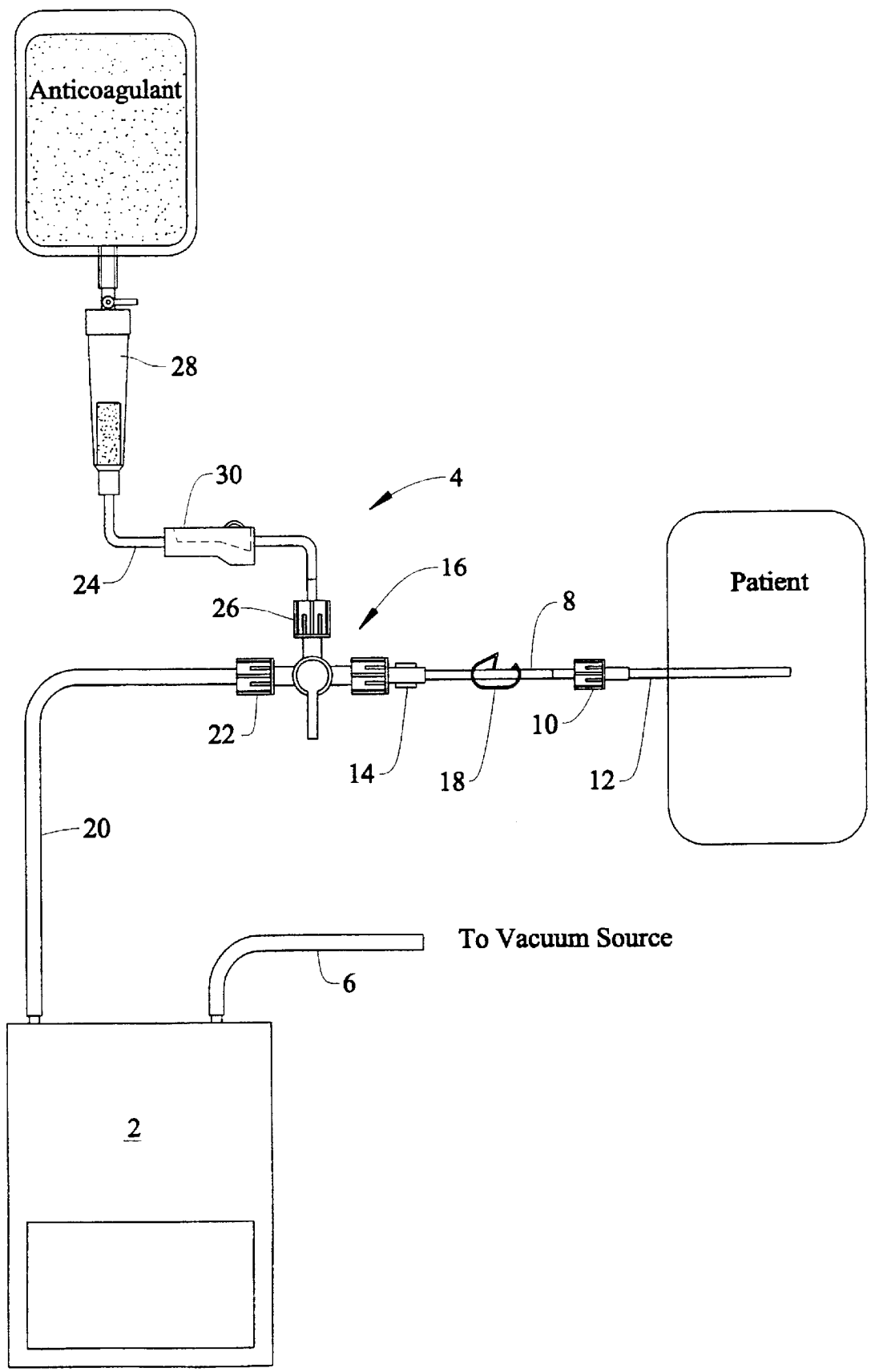

SYSTEM FOR WITHDRAWAL OF BLOOD

CROSS REFERENCE TO RELATED APPLICATION

This application claims the benefit of U.S. Provisional Patent Application Ser. No. 60/087,398, which was filed on Jun. 1, 1998.

BACKGROUND

In surgical procedures where significant blood loss may occur making it necessary to provide replacement blood to the patient, it has been found desirable to withdraw some of the patient's blood and replace the volume of the blood withdrawn with a crystallized solution. This process, done just before the surgery, is generally known as hemodilution, and has developed based on recognition that the oxygen-carrying capacity of stored blood is greatly reduced and, further, that it contains metabolic products, which must be processed by the patient after transfusion. Hemodilution and use of the patient's own blood that was withdrawn just before surgery to replace the blood lost during surgery has been found to provide better perfusion and reduced blood loss due to the dilution of the patient's blood.

In prior hemodilution processes, the blood is withdrawn by draining it into a bag using only the patient's venous pressure and the gravity head pressure naturally available by placing the bag below the patient. The flow rate attainable by this procedure is, however, very low, and the process requires too long, consuming expensive Operating Room time.

SUMMARY OF THE INVENTION

In accordance with the invention, the patient's blood is withdrawn more quickly by applying a precisely-controlled vacuum. By this technique, the time required for withdrawal of a given volume of blood is reduced by more than one-half, when compared to the prior art, gravity technique, and there is no measurable damage to the withdrawn blood.

In accordance with a method of the invention, a patient's circulatory system is connected to a canister maintained at a vacuum controlled to be approximately −100 mm ±20 mm Hg. This level of vacuum allows the blood to be withdrawn very quickly and efficiently and avoids damage to the withdrawn blood or to the patient.

A preferred apparatus in accordance with the invention includes a tubing set for connecting the canister to a catheter access to the patient's circulatory system, or to a needle. The tubing set includes a first tube section for connection to the catheter access or needle, a second tube section with a bag-piercing spike for connection to a source of anticoagulant, a third tube section for connection to the canister, and a stopcock joining the three tube sections for mixing anticoagulant with withdrawn blood and controlling the flows of the fluids in the three tubes. "Tube" as used here is intended to refer to any sort of device for carrying fluids. In the preferred embodiment, the tubes are flexible tubes of physiologically compatible materials normally used in medical procedures.

The vacuum level, tubing sizes, e.g., the internal diameter (ID) and tubing length, are balanced so that the forces resulting from application of the vacuum to the patient's circulatory system do not collapse the patient's vein, but still provide pressure low enough to speed the withdrawal of venous blood. A vacuum that is too high and/or tubing and fittings that are too large would result in application of too much vacuum, and the resulting vein collapse would reduce or halt the flow. A vacuum that is too low, tubing and fitting that are too small in internal diameter, or tubing that is too long would not provide adequate reduced flow rate, extending blood collection time. Further, the relative sizes of the tubing and fittings connected to the patient and the tubing and fittings connected to the anticoagulant ensure that the proper amount of anticoagulant is mixed with the withdrawn blood and eliminate the possibility that anticoagulant will flow into the patient.

BRIEF DESCRIPTION OF THE DRAWING FIGURE

The drawing FIGURE illustrates a tubing set in accordance with the invention.

DETAILED DESCRIPTION OF THE PREFERRED EMBODIMENT.

With reference to the drawing FIGURE, an apparatus in accordance with the invention primarily includes a blood collection canister 2 and a tubing set 4.

The canister 2 is connected to a vacuum source (not illustrated) by a conduit 6. The vacuum source is controlled such that the vacuum level in the preferred embodiment is −100 mm Hg ±90 mm Hg. The vacuum system must provide careful control and in the preferred embodiment is that disclosed in international patent application serial number PCT/US96/16771 and sold under the trademark "Bloodstream." Such a system uses a feed-back circuit to measure the vacuum in the collection canister continually and to maintain a constant vacuum level. Use of the continuous vacuum as disclosed herein is preferable to the decaying vacuum of prior systems because it provides the maximum withdrawal rate. Further, applicant's have found that the low vacuum level significantly reduces damage to the blood during withdrawal, resulting in higher-quality blood for return to the patient.

The tubing set 4 comprises a first flexible tube 8 that has a luer lock fitting 10 for connection to a needle or catheter 12, which provides access to the circulatory system of a patient. This first tube 8 is short. e.g., approx. 6" long. The tube 8 includes a second luer lock 14 for connecting the tube to a mixing and control valve, such as a stopcock 16. Further, the tube 8 is provided with a clamp 18 for occluding the tube when disconnection is desired. In the preferred embodiment, the diameter of the tubing 8 is approximately 0.124" to 0.130", and the luer locks are large bore (0.100" ID min) so that resistance to blood flow is minimized.

The stopcock 16 mixes the stream of anticoagulant with the stream of withdrawn blood and provides on/off flow control of the fluids. The stopcock preferably has a large bore (0.100" ID min) to reduce flow restrictions.

A second tubing 20, which is connected at one end to the stopcock by a luer connector 22 and to the collection canister at the other has a larger ID (e.g., 0.184" to 0.190" ID) than the patient connection tubing 8 and is substantially longer (approx. 84.0"). The larger ID is desirable for at least three reasons: (1) it reduces resistance to flow over the longer length, (2) it reduces resistance to flow due to the increasing viscosity of the blood as it cools in the line, and (3) it compensates for the increased volume caused by the addition of anticoagulant to the withdrawn blood at the stopcock.

The third tube 24 is smaller than the other two tubes and carries anticoagulant. This tube is connected to the stopcock 16 at one end by a luer lock 26, and the other end of the tube is fitted with a bag spike 28 of known design having a drip chamber and a filter. The tube 24 is preferably fitted with a flow control device, such as a roller clamp 30, burette, roller pump or the like to provide independent control of the anticoagulant flow.

The careful balance among vacuum level, tubing diameters, and tubing length is important to achieving the correct performance of the device and provides performance that is significantly better than prior devices. Thus, the anticoagulant line is smaller than tube 8 to remove the possibility that anticoagulant will flow into the patient through tube 8, should the bag of anticoagulant be placed far enough above the patient to create a large pressure head. Similarly, the diameter of the tube 20 is large enough that the anticoagulant and withdrawn blood naturally flow toward the canister 2.

The stopcock 16 is used to mix and control the flow of fluids during setup and operation. The stopcock may be replaced by a variety of devices that perform these functions, for example, a T-connector and a clamp for each of the tubes. When a stopcock is used, it may be placed in one of three positions. In the first position, flow through tube 8 is blocked, a position that would be used during set-up or after completion of blood withdrawal. In a second position, flow through the anticoagulant tube 24 is blocked, a position that would be used, for example, during change of anticoagulant bags. In a third position, flow is permitted in all of the tubes, whereby the vacuum in the canister withdraws blood from the patient and, simultaneously, draws anticoagulant into the withdrawn blood. The anticoagulant is thoroughly mixed with the blood during passage through the tube 20, efficiently treating the blood and eliminating the necessity of providing additional anticoagulant in the canister 2.

The tubing set 4, comprising the three tubes 8, 20, and 24 connected by the flow control device 16, is preferably supplied as a separate, sterile disposable unit to ensure safety. The canister 2 may also be a part of this set but is preferably a component of the separate vacuum system.

In operation, the blood withdrawal set is used by attaching the tube 8 to the needle 12, the tube 24 to a bag of anticoagulant, and the tube 20 to the canister. During set-up, the stopcock will be placed in a position whereby it blocks flow from the patient, and the vacuum system may be activated before or after connection of the three tubes. After attaching the set to the patient, the stopcock is placed in the position whereby all tubes are in communication with each other, allowing blood and anticoagulant to be drawn into the canister.

It will be appreciated that while it is usually desired to withdraw venous blood, the system may also be used to withdraw arterial blood.

Modifications within the scope of the appended claims will be apparent to those of skill in the art.

We claim:

1. A method for withdrawing blood from a patient comprising the steps of providing a tubing set comprising a mixing connector, a first tube adapted to be removably connected at one end to a catheter providing access to a patient's circulatory system and connected to said mixing connector at its opposed end, a second tube adapted to be removably connected to a vacuum canister at one end and connected to said mixing connector at its opposite end, and a third tube adapted to be removably connected to a container of anticoagulant at one end and connected to said mixing connector at its opposite end, connecting said second tube to said canister, placing said first tube in fluid communication with the circulatory system of said patient, and applying a controlled vacuum to said canister.

2. A method according to claim 1 further comprising the step of placing anticoagulant in fluid communication with said canister whereby said anticoagulant is mixed with blood withdrawn from said patient.

3. A method according to claim 2 wherein the resistance to fluid flow of said first tube is greater than that of said second tube.

4. A method according to claim 3 wherein the inner diameter of said first tube is smaller than that of said second tube.

5. A method according to claim 1 wherein said controlled vacuum is about −100 mm Hg.

6. Apparatus for withdrawal of blood from a patient comprising a mixing connector, a first tube adapted to be connected at one end to a catheter providing access to a patient's circulatory system and connected to said mixing connector at its opposed end, a second tube adapted to be connected to a vacuum canister at one end and connected to said mixing connector at its opposite end, and a third tube adapted to be connected to a container of anticoagulant at one end and connected to said mixing connector at its opposite end, wherein said mixing connector selectively admits fluids in said first and third tubes into said second tube simultaneously or prevents flow of fluids in said first or third tubes into said second tube, the internal diameter of said first tube is less than that of said second tube, and said second tube is longer than said first tube.

7. Apparatus according to claim 6 wherein said mixing connector has two inlets in fluid communication with an outlet, said first and third tubes are connected to respective inlets, and said second tube is connected to said outlet.

8. Apparatus according to claim 7 wherein said mixing connector is adapted to allow simultaneous flow of fluids from said inlets to said outlet or selectively to block fluid flow from either of said inlets.

9. Apparatus according to claim 6 wherein said mixing connector is a three-position stopcock.

10. Apparatus according to claim 6 further comprising said canister, wherein said canister is maintained at a vacuum of about −100 mm Hg.

11. Apparatus according to claim 6 wherein the internal diameter of said first tube is about 0.124 inch to about 0.130 inch.

12. Apparatus according to claim 11 wherein the internal diameter of said second tube is about 0.184 inch to about 0.190 inch.

13. Apparatus according to claim 12 wherein the length of said second tube is at least about 84 inches.

* * * * *

UNITED STATES PATENT AND TRADEMARK OFFICE
CERTIFICATE OF CORRECTION

PATENT NO. : 6,508,778 B1
DATED : January 21, 2003
INVENTOR(S) : Verkaart et al.

It is certified that error appears in the above-identified patent and that said Letters Patent is hereby corrected as shown below:

<u>Title page,</u>
Insert -- PCT Filed:      June 1, 1999

[86] PCT No.:            PCT/US99/10485

§ 371 (c)(1),
(2), (4) Date:           November 29, 2000

[87] PCT Pub. No.:       WO99/62583

PCT Pub. Date:           December 9, 1999 --

Signed and Sealed this

Twenty-ninth Day of July, 2003

JAMES E. ROGAN
*Director of the United States Patent and Trademark Office*